United States Patent [19]

Reissenweber et al.

[11] Patent Number: 4,469,884

[45] Date of Patent: Sep. 4, 1984

[54] PREPARATION OF N-METHOXY-N-METHYLURETHANES

[75] Inventors: Gernot Reissenweber, Boehl-Iggelheim; Ulrich Schirmer, Heidelberg, both of Fed. Rep. of Germany

[73] Assignee: BASF Aktiengesellschaft, Fed. Rep. of Germany

[21] Appl. No.: 484,886

[22] Filed: Apr. 14, 1983

[30] Foreign Application Priority Data

Apr. 14, 1982 [DE] Fed. Rep. of Germany ....... 3213684

[51] Int. Cl.$^3$ .......................................... C07C 125/065
[52] U.S. Cl. .................................................... 560/160
[58] Field of Search ......................................... 560/160

[56] References Cited

PUBLICATIONS

Sandler, "Organic Functional Group Preparations, vol. III, pp. 321–327, 339–344, (1972).
A. T. Fuller and H. King, J. Chem. Soc. (London), 1947, 963.
R. T. Major and E. E. Fleck, Am. Soc. 50, (1928), 1479.

*Primary Examiner*—Michael L. Shippen
*Attorney, Agent, or Firm*—Keil & Weinkauf

[57] ABSTRACT

N-Methoxy-N-methylurethanes are prepared by a process in which first (1) hydroxylamine is converted with an alkyl chloroformate to the corresponding N-hydroxyurethane, then (2) this product is reacted with a methylating agent to give the N-methoxy-N-methylurethane, and finally (3) the N-methoxy-N-methylurethane is isolated. In this process, first, (1) while maintaining a certain temperature and a certain pH, (1.1) an aqueous solution of an inorganic hydroxylammonium salt is mixed thoroughly with (1.2) an equimolar amount of an alkyl chloroformate, then (2) while maintaining a certain temperature and a certain pH, (2.1) a mixture comprising (2.1.1) the reaction mixture obtained as described in (1), (2.1.2) a water-insoluble organic solvent and (2.1.3) a phase-transfer catalyst is mixed thoroughly with (2.2) a water-insoluble methylating agent which is soluble in the solvent under (2.1.2), and the resulting mixture is kept at a certain temperature for a certain time, and finally (3) any methylating agent still present in the reaction mixture obtained as described in (2) is destroyed, the non-aqueous liquid phase is separated off from the mixture thus treated, and the N-methoxy-N-methylurethane is isolated from this phase by stripping off the solvent. A relatively pure product is obtained in high yield.

1 Claim, No Drawings

PREPARATION OF N-METHOXY-N-METHYLURETHANES

The present invention relates to a process for the preparation of N-methoxy-N-methylurethanes in which first (1) hydroxylamine is converted with an alkyl chloroformate to the corresponding N-hydroxyurethane, then (2) this product is reacted with a methylating agent to give the N-methoxy-N-methylurethane, and finally (3) the N-methoxy-N-methylurethane is isolated.

Processes of this type have been disclosed, and for a typical process reference may be made to A. T. Fuller and H. King, J. Chem. Soc. 1947, 963 and to R. T. Major and E. E. Fleck, Am. Soc. 50, (1928), 1479.

The preparation of N-methoxy-N-methylurethanes by the conventional procedures is unsatisfactory in a number of respects, in particular for economical preparation on an industrial scale. Thus, for example, the individual steps (1), (2) and (3) have to be carried out as separate operations in separate apparatuses; moreover, the yields in step (1) and in particular in step (2) are moderate, while in step (3), which is designed as a distillation, there is a danger of explosive decomposition. An attempt to repeat the process described by Fuller and King gave, after two unsuccessful attempts, a yield of about 60% and a purity of from 85 to 90%, and hence did not reach the value of 94% stated by the earlier workers.

It is an object of the present invention to provide a process of the type defined at the outset, which does not have the above disadvantages.

We have found that this object is achieved if steps (1), (2) and (3) are carried out in a continuous operation, with the provisos that step (2) is carried out in a two-phase system comprising a liquid aqueous phase and a liquid non-aqueous phase, using a phase-transfer catalyst, and in step (3) the N-methoxy-N-methylurethane is isolated by extraction.

The present invention accordingly relates to a process for the preparation of N-methoxy-N-methylurethanes, in which first (1) hydroxylamine is converted with an alkyl chloroformate to the corresponding N-hydroxyurethane, then (2) this product is reacted with a methylating agent to give the N-methoxy-N-methylurethane, and finally (3) the N-methoxy-N-methylurethane is isolated. In the process according to the invention, first, (1) while constantly maintaining a temperature of from $-10°$ to $20°$ C., preferably from $0°$ to $10°$ C., and a pH of from 2 to 7, preferably from 4.5 to 6.5, (1.1) a 0.5–3, preferably 1–2, molar aqueous solution of an inorganic hydroxylammonium salt is mixed vigorously and thoroughly with (1.2) an equimolar amount of an alkyl chloroformate, then, (2) while constantly maintaining a temperature of from $10°$ to $50°$ C., preferably from $20°$ to $40°$ C., and a pH of from 7 to 14, preferably from 8.5 to 13.5, (2.1) a mixture comprising
(2.1.1) 100 parts by volume of the reaction mixture obtained as described in (1),
(2.1.2) from 10 to 50, preferably from 15 to 30, parts by volume of a water-insoluble organic solvent and
(2.1.3) from 0.1 to 2, preferably from 0.2 to 0.5, mole-%, based on the N-hydroxyurethane present in the reaction mixture under (2.1.1), of a phase-transfer catalyst is mixed vigorously and thoroughly with (2.2) from 100 to 150, preferably from 100 to 120, equivalent-%, based on the N-hydroxyurethane present in the reaction mixture under (2.1.1), of a water-insoluble methylating agent which is soluble in the solvent under (2.1.2), and the resulting mixture is kept at from $10°$ to $50°$ C., preferably from $20°$ to $40°$ C., for from 1 to 5, preferably from 2 to 3, hours, and finally (3) any methylating agent still present in the reaction mixture obtained as described in (2) is destroyed, the non-aqueous liquid phase (extract) is separated off from the mixture thus treated, and the N-methoxy-N-methylurethane is isolated from this phase by stripping off the solvent.

The novel process permits the preparation of N-methoxy-N-methylurethanes in high yield and good industrial purity by a safe procedure. N-Methoxy-N-methylurethanes are known to be useful intermediates, for example in the preparation of herbicides.

Regarding the process according to the invention, the following may be stated specifically:

The process can be carried out without difficulty by those skilled in the art. The apparatuses also present no problems: the process can, for example, be carried out directly in a conventional stirred apparatus which is equipped with a cooling or heating device and possesses means of feeding in and conducting away liquids or gases.

In carrying out step (1), it has proved advantageous initially to introduce the aqueous solution (1.1) of the inorganic hydroxylammonium salt, which can be, in particular, a sulfate, and then to establish the desired pH; the latter may be achieved most economically by adding an aqueous caustic alkali solution, in particular sodium hydroxide solution. The further procedure is then advantageously carried out by gradually adding the alkyl chloroformate (1.2), which is preferably a $C_1$–$C_4$-alkyl ester, in particular the methyl or ethyl ester, to the vigorously stirred solution, the temperature being kept at the required value by cooling and the pH being kept at the required value by continuous addition of an aqueous base, preferably a caustic alkali solution, in particular sodium hydroxide solution.

In step (2), it is advantageous first to prepare the mixture (2.1) comprising the reaction mixture (2.1.1) obtained as described in (1), the water-insoluble organic solvent (2.1.2) and the phase-transfer catalyst (2.1.3). The solvent (2.1.2) and the catalyst (2.1.3) may be the appropriate conventional ones. Examples of suitable solvents (2.1.2) are, in particular, chlorohydrocarbons, such as methylene chloride, chloroform, carbon tetrachloride, 1,2-dichloroethane and mixtures of these, and aliphatic-aromatic hydrocarbons, such as toluene, ethylbenzene, o-, m- and p-xylene, isopropylbenzene and mixtures of these. Particularly suitable phase-transfer catalysts (2.1.3) are quaternary ammonium salts, eg. N,N-dibenzyl-N,N-dimethylammonium chloride, N-benzyl-N,N,N-trimethylammonium chloride, N-benzyl-N,N,N-triethylammonium chloride and N-dodecyl-N,N,N-trimethylammonium chloride, and quaternary phosphonium salts, eg. tetraphenylphosphonium bromide.

After the mixture (2.1) has been prepared, in general it is brought to the temperature chosen for the further reaction and to the selected pH; the latter operation may be carried out as described in step (1). The further procedure can then be carried out successfully by adding the methylating agent (2.2) while stirring vigorously, and, in the further procedure, keeping the temperature and the pH at the required values; the latter may once again be achieved by continuous addition of an aqueous base. Regarding the composition, it may be stated that the methylating agent can be an appropriate conventional one, ie. especially dimethyl sulfate or even a methyl halide, eg. methyl chloride, bromide or iodide. The same applies to the base: for economic reasons, this is primarily sodium hydroxide solution, but sodium carbonate may also be used. After the mixture (2.1) and the methylating agent (2.2) have been combined, the resulting mixture is then kept at the required temperature for the required time, advantageously with further vigorous stirring.

In step (3), the N-methoxy-N-methylurethane formed in step (2) is worked up. To do this, any methylating agent still present in the reaction mixture is first destroyed by reaction with an agent conventionally used for this purpose. This agent is advantageously chosen so that a water-soluble reaction product results, as is the case, in particular, where ammonia or ammonia water is used. Thereafter, the non-aqueous liquid phase is separated off from the reaction mixture and, if desired, is washed with water, the solvent is stripped off and the desired N-methoxy-N-methylurethane is obtained as the residue.

EXAMPLE

The procedure was carried out using a conventional stirred apparatus which had an effective volume of 120 liters, was equipped with a cooling or heating device and possessed means of feeding in and conducting away liquids or gases.

(1) First step of the process 40 liters of a 0.875 molar aqueous solution of hydroxylammonium sulfate were initially introduced into the apparatus, and the pH was brought to 6.5 by the addition of 1.2 liters of a 19 molar aqueous sodium hydroxide solution. Thereafter, 7.8 kg, ie. the stoichiometric amount, of 98% pure ethyl chloroformate were added to the vigorously stirred mixture in the course of 150 minutes, while the temperature was constantly maintained at 0°–10° C. by cooling. At the same time, the pH was constantly kept at 6.0–6.8 by continuously adding 19 molar aqueous sodium hydroxide solution (a total of 7.5 liters).

(2) Second step of the process 20 liters (=33 parts by volume) of methylene chloride and, as the phase-transfer catalyst, 50 g (=0.3 mole-%, based on the N-hydroxyurethane present in the reaction mixture) of benzyltriethylammonium chloride were added to the reaction mixture which was obtained as described in (1) and had a volume of about 60 liters (=100 parts by volume). Thereafter, the mixture was brought to 20° C., while stirring vigorously. 18.9 kg (=110 equivalent-%, based on the N-hydroxyurethane present in the reaction mixture) of dimethyl sulfate were then added to the vigorously stirred mixture in the course of 120 minutes, while the temperature was constantly maintained at 20°–35° C. by cooling. At the same time, the pH was constantly kept at 8.5–13.5 by continuously adding 19 molar aqueous sodium hydroxide solution (a total of 7.5 liters). The entire mixture was then kept at 30° C. for a further 3 hours, vigorous stirring being continued.

(3) Third step of the process

To destroy any methylating agent still present, 5 liters of 3 molar ammonia water were added to the vigorously stirred reaction mixture obtained as described in (2), and the mixture was then allowed to stand. The non-aqueous liquid phase which separated out as the lower phase during standing was removed and washed with 20 liters of water, and the solvent was stripped off at a maximum temperature of 50° C. 7.45 kg (yield: 80%, based on ethyl chloroformate) of 96% pure N-methoxy-N-methylurethane (ethyl N-methoxy-N-methylcarbamate) were obtained.

We claim:

1. A process for the preparation of an N-methoxy-N-methylurethane, in which first (1) hydroxylamine is converted with an alkyl chloroformate to the corresponding N-hydroxyurethane, then (2) this product is reacted with a methylating agent to give the N-methoxy-N-methylurethane, and finally (3) the N-methoxy-N-methylurethane is isolated, wherein first, (1) while constantly maintaining a temperature of from −10° to 20° C. and a pH of from 2 to 7,
   (1.1) a 0.5–3 molar aqueous solution of an inorganic hydroxylammonium salt is mixed vigorously and thoroughly with
   (1.2) an equimolar amount of an alkyl chloroformate, then,
(2) while constantly maintaining a temperature of from 10° to 50° C. and a pH of from 7 to 14,
   (2.1) a mixture comprising
      (2.1.1) 100 parts by volume of the reaction mixture obtained as described in (1),
      (2.1.2) from 10 to 50 parts by volume of a water-insoluble organic solvent and
      (2.1.3) from 0.1 to 2 mole-%, based on the N-hydroxyurethane present in the reaction mixture under (2.1.1), of a phase-transfer catalyst, is mixed vigorously and thoroughly with
   (2.2) from 100 to 150 equivalent-%, based on the N-hydroxyurethane present in the reaction mixture under (2.1.1), of a water-insoluble methylating agent which is soluble in the solvent under (2.1.2),
   and the resulting mixture is kept at from 10° to 50° C. for from 1 to 5 hours, and finally,
(3) any methylating agent still present in the reaction mixture obtained as described in (2) is destroyed, the non-aqueous liquid phase is separated off from the mixture thus treated, and the N-methoxy-N-methylurethane is isolated from this phase by stripping off the solvent.

* * * * *